United States Patent
Thomsen et al.

(10) Patent No.: US 12,023,043 B2
(45) Date of Patent: Jul. 2, 2024

(54) MICROFRACTURE PICK SYSTEMS AND ASSOCIATED SURGICAL METHODS

(71) Applicant: ARTHREX, INC., Naples, FL (US)

(72) Inventors: Darren W. Thomsen, Naples, FL (US); Zachary Day, Naples, FL (US); Thomas O. Clanton, Vail, CO (US)

(73) Assignee: ARTHREX, INC., Naples, FL (US)

( * ) Notice: Subject to any disclaimer, the term of this patent is extended or adjusted under 35 U.S.C. 154(b) by 440 days.

(21) Appl. No.: 17/345,013

(22) Filed: Jun. 11, 2021

(65) Prior Publication Data
US 2021/0386432 A1  Dec. 16, 2021

Related U.S. Application Data

(60) Provisional application No. 63/037,849, filed on Jun. 11, 2020.

(51) Int. Cl.
*A61B 17/16* (2006.01)
*A61B 17/92* (2006.01)

(52) U.S. Cl.
CPC .... *A61B 17/1604* (2013.01); *A61B 2017/922* (2013.01)

(58) Field of Classification Search
CPC ............ A61B 17/1604; A61B 2017/922
See application file for complete search history.

(56) References Cited

U.S. PATENT DOCUMENTS

| | | | | |
|---|---|---|---|---|
| 8,721,648 B2* | 5/2014 | Meridew | ............ | A61B 17/1668 606/89 |
| 9,259,230 B2* | 2/2016 | Rogers | ............... | A61B 17/1604 |
| 9,393,030 B2* | 7/2016 | Meridew | ............ | A61B 17/1664 |
| 11,304,708 B2* | 4/2022 | Alfonso | ............ | A61B 17/1675 |
| 2007/0270870 A1* | 11/2007 | Torrie | ................ | A61B 17/1666 606/86 R |
| 2012/0290020 A1* | 11/2012 | Meridew | ............ | A61B 17/1742 606/86 R |
| 2014/0336656 A1* | 11/2014 | Rogers | ............... | A61B 17/1604 606/83 |

OTHER PUBLICATIONS

Smith & Nephew Food and Ankle Instrument Set, Ordering Information, two pages.

* cited by examiner

*Primary Examiner* — Zade Coley
(74) *Attorney, Agent, or Firm* — Carlson, Gaskey & Olds, P.C.

(57) ABSTRACT

Exemplary microfracture pick systems may include a microfracture pick, a strike plate, and a punch extension. The strike plate may be secured to a handle of the microfracture pick, and the punch extension is connectable to the strike plate. The punch extension is configured to apply an "off-axis" impact force to the microfracture pick. The "off-axis" impact force is generally aligned with an axis of a strike tip of the microfracture pick, thereby substantially preventing the strike tip from skiving across a bone surface during surgical uses.

17 Claims, 5 Drawing Sheets

MICROFRACTURE PICK SYSTEMS AND ASSOCIATED SURGICAL METHODS

CROSS-REFERENCE TO RELATED APPLICATIONS

This disclosure claims priority to U.S. Provisional Application No. 63/037,849, filed on Jun. 11, 2020, the entire disclosure of which is incorporated herein by reference.

BACKGROUND

This disclosure relates to the field of surgery, and more particularly to microfracture pick systems and associated surgical methods.

Microfracture surgery is an articular cartilage repair procedure performed by creating small fractures in underlying bone in order to stimulate the growth of fibrocartilage. A microfracture pick may be used to create the small fractures in the underlying bone.

SUMMARY

This disclosure relates to microfracture pick systems for performing microfracture surgical procedures. The microfracture pick systems may be used to create microfractures in a bone surface.

An exemplary microfracture pick system may include, inter alia, a microfracture pick, a strike plate securable to a handle of the microfracture pick, and a punch extension connectable to the strike plate. The punch extension is configured to apply an impact force to a portion of the microfracture pick.

An exemplary surgical method may include, inter alia, securing a strike plate to a handle of a microfracture pick, securing a punch extension to the strike plate, and striking the punch extension, thereby applying an off-axis impact force to the microfracture pick for forming a microfracture in a bone surface.

DETAILED DESCRIPTION

This disclosure is directed to microfracture pick systems for performing microfracture surgical procedures. The microfracture pick systems may be used to create microfractures in a bone surface. Blood may flow within the created microfractures and then clot to form fibrocartilage, thereby repairing articular cartilage associated with the bone surface.

An exemplary microfracture pick system may include a microfracture pick, a strike plate, and a punch extension. The strike plate may be secured to a handle of the microfracture pick, and the punch extension is connectable to the strike plate. The punch extension is configured to apply an "off-axis" impact force to the microfracture pick. The "off-axis" impact force is generally aligned with an axis of a strike tip of the microfracture pick, thereby substantially preventing the strike tip from skiving across a bone surface during surgical use.

An exemplary surgical method may include securing a strike plate to a handle of a microfracture pick, securing a punch extension to the strike plate, and striking the punch extension, thereby applying an off-axis impact force to the microfracture pick for forming a microfracture in a bone surface. These and other features of this disclosure are described in further detail below.

Figure 1:
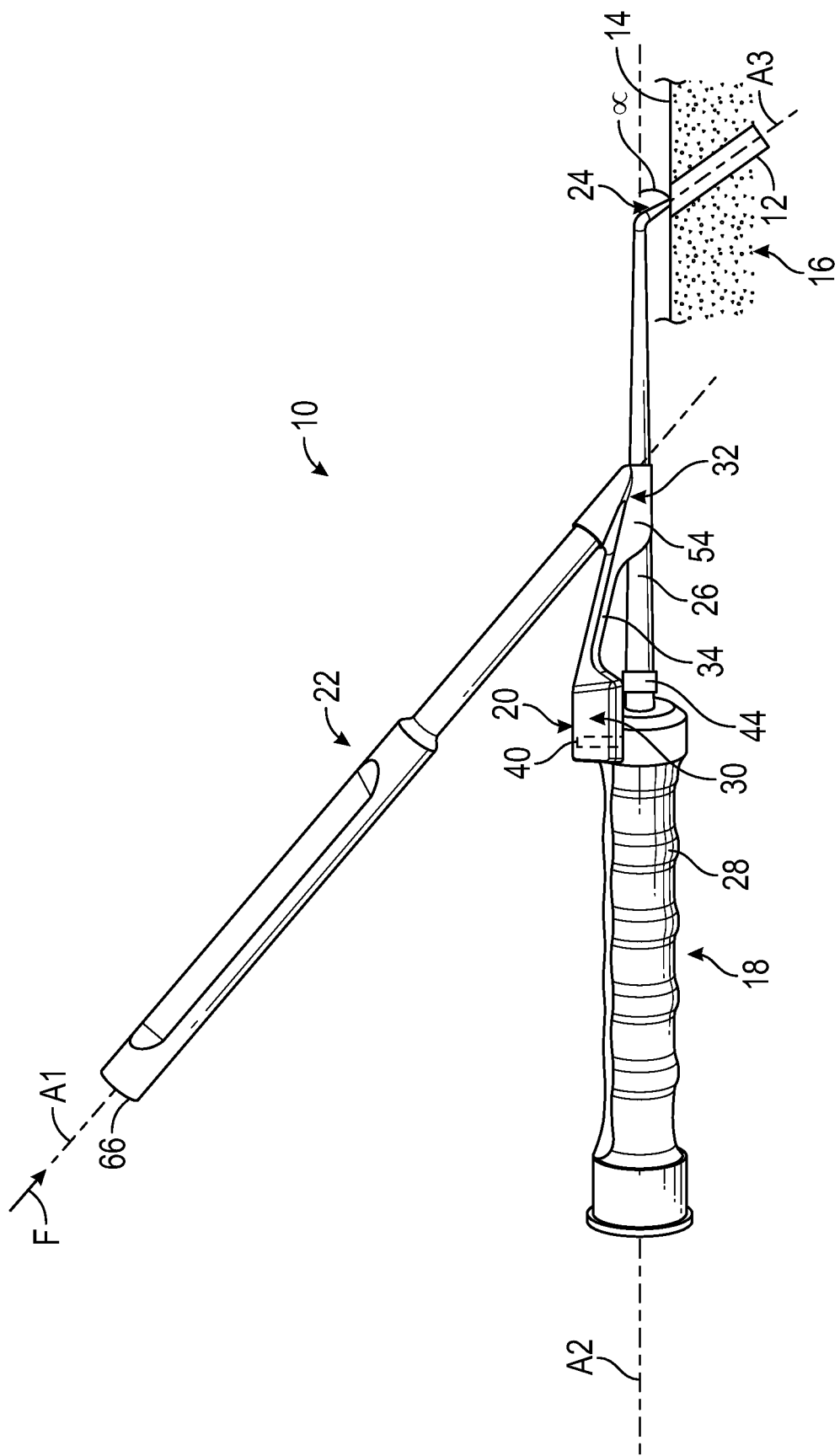
FIG. 1 is an assembled view of a microfracture pick system for performing microfracture surgical methods.
Figure 2:
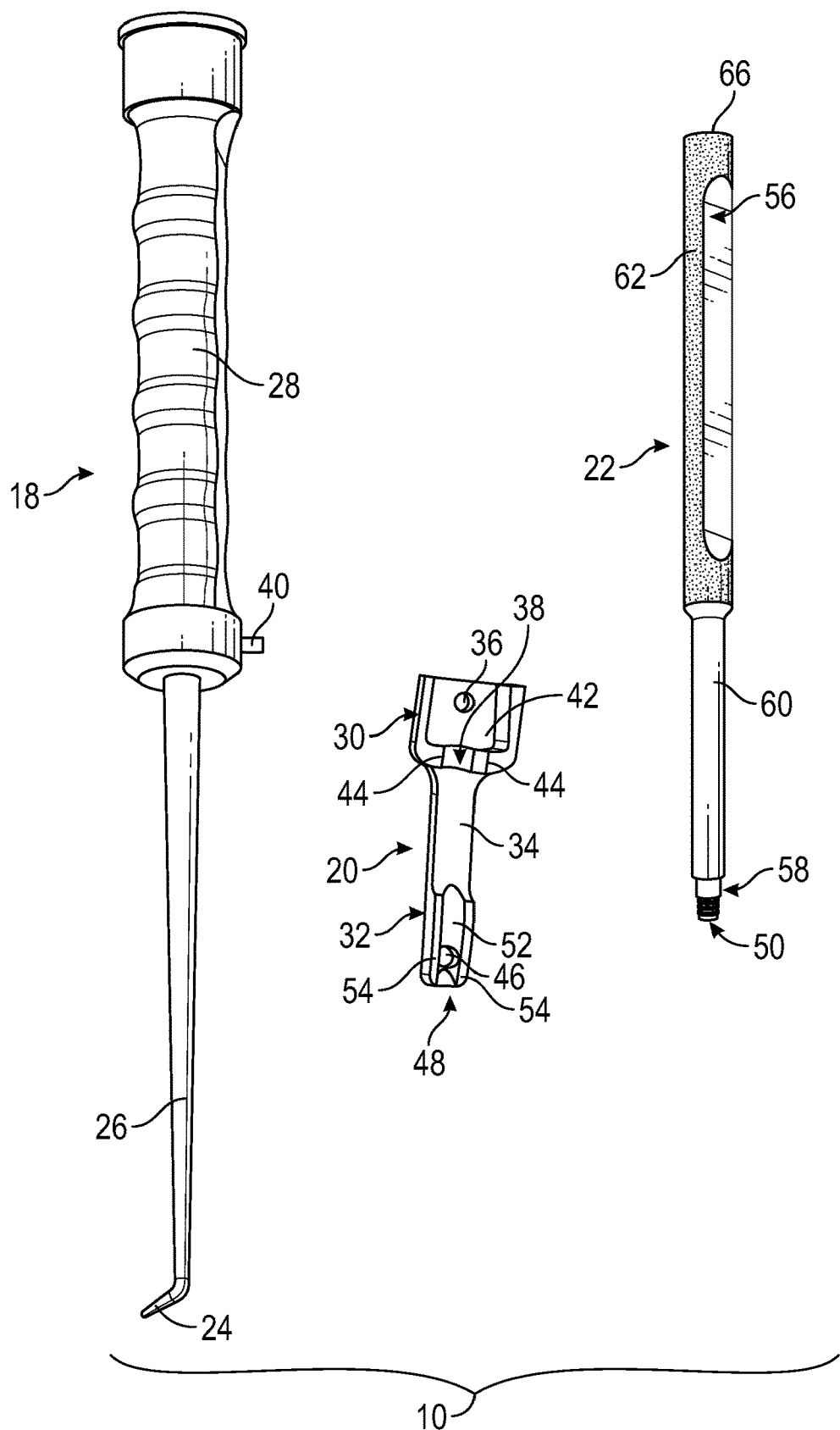
FIG. 2 is a disassembled view of the microfracture pick system of FIG. 1.

FIGS. 1-2 illustrate an exemplary microfracture pick system 10 for creating microfractures 12 (e.g., relatively small perforations, channels, etc.) in a bone surface 14 during a surgical method, such as a microfracture surgical procedure. The bone surface 14 may by any bone surface associated with any bone of the human musculoskeletal system. The microfractures 12 are typically created in the bone surface 14 near an area of removed cartilage and extend a relatively short distance (e.g., 2 to 5 mm) into subchondral bone 16 underlying the bone surface 14. Blood may flow within the created microfractures 12. The blood can eventually clot to form fibrocartilage, thereby repairing the articular cartilage.

The microfracture pick system 10 may include a microfracture pick 18, a strike plate 20, and a punch extension 22. The strike plate 20 is connectable to the microfracture pick 18, and the punch extension 22 is connectable to the strike plate 20. An impact force F may be applied to the punch extension 22 to drive a strike tip 24 of the microfractrue pick 18 through the bone surface 14 and into the underlying subchondral bone 16. The impact force F may be transferred from the punch extension 22, through the strike plate 20, through a shaft 26 of the microfracture pick 18, and then to the strike tip 24 to drive the strike tip 24 through the bone surface 14 for forming the microfractures 12.

The punch extension 22 extends along a longitudinal centerline axis A1 once connected to the strike plate 20. The impact force F may be applied along the longitudinal centerline axis A1 of the punch extension 22. The longitudinal centerline axis A1 is transverse (e.g., non-perpendicular) to a longitudinal centerline axis A2 of the microfractrue pick 18. The impact force F may therefore be considered to be applied "off-axis" relative to the microfracture pick 18. The advantage of such an "off-axis" arrangement is that the impact force F is substantially axially aligned with a longitudinal centerline axis A3 of the strike tip 24 when forming the microfractures 12. Therefore, the risk of the strike tip 24 skiving across the bone surface 14 during use of the microfracture pick system 10 is substantially reduced.

Figure 3:
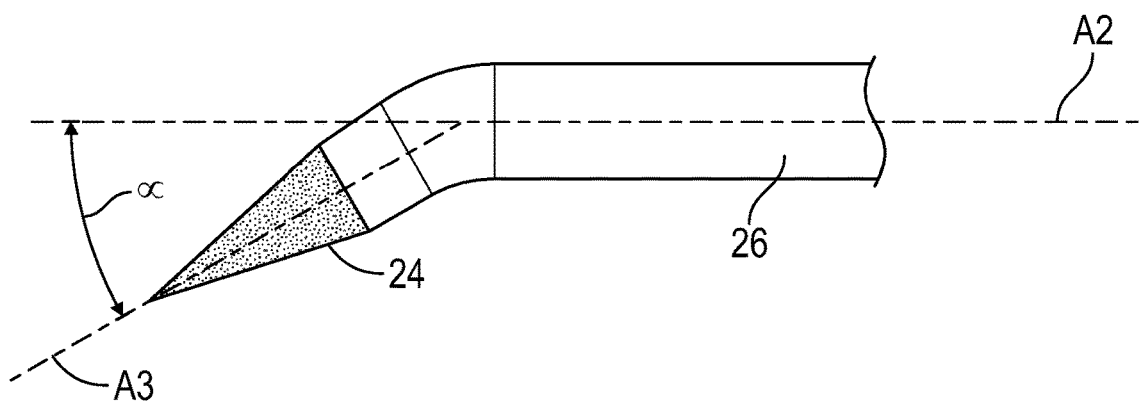
FIG. 3 illustrates an exemplary strike tip of a microfracture pick of a microfracture pick system.
Figure 4:
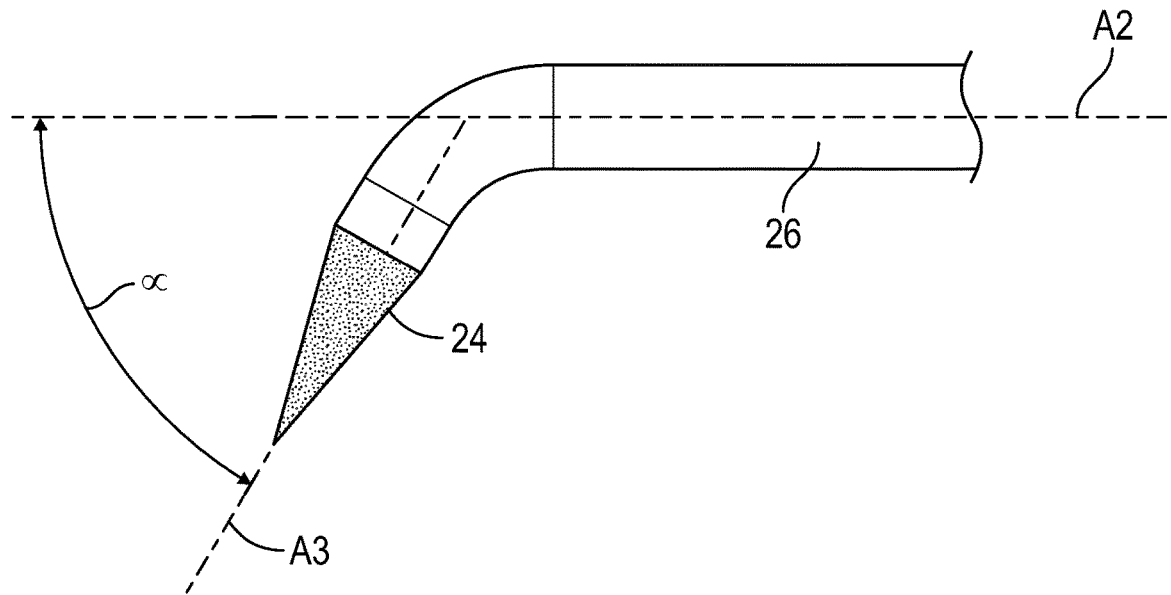
FIG. 4 illustrates another exemplary strike tip of a microfracture pick of a microfracture pick system.
Figure 5:
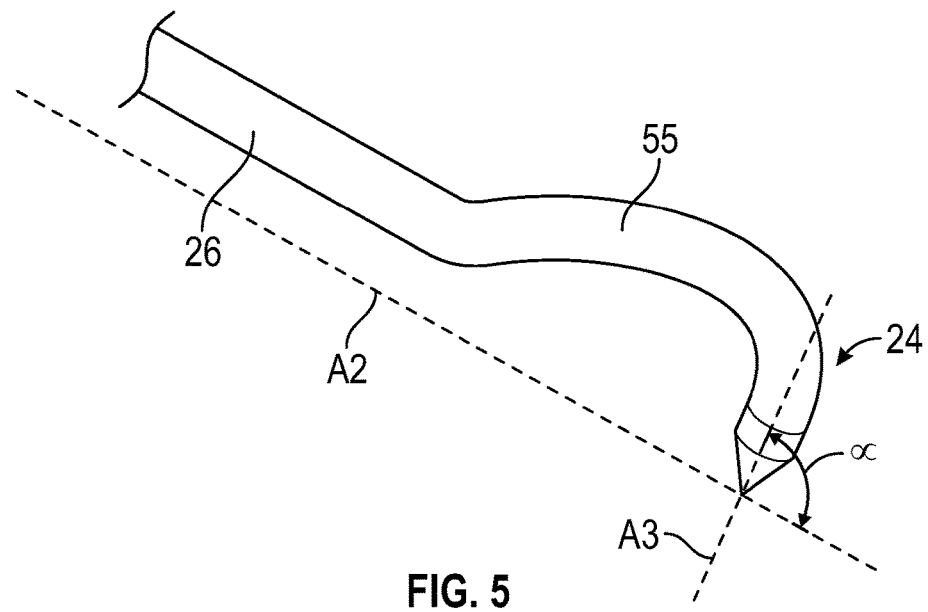
FIG. 5 illustrates yet another exemplary strike tip of a microfracture pick of a microfracture pick system.
Figure 6A:
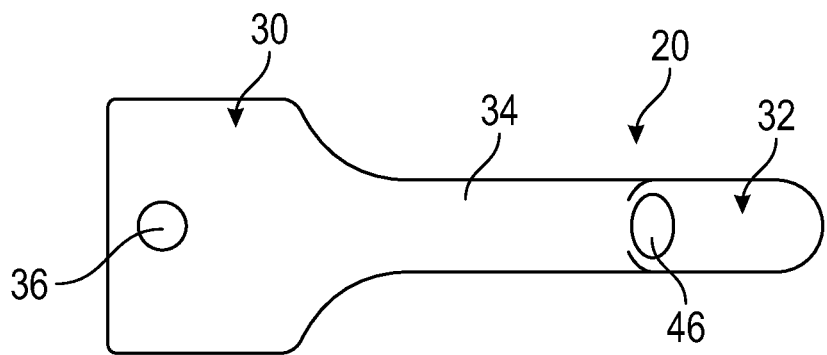
FIGS. 6A, 6B, 6C, 6D, and 6E illustrate an exemplary strike plate of a microfracture pick system.
Figure 6B:
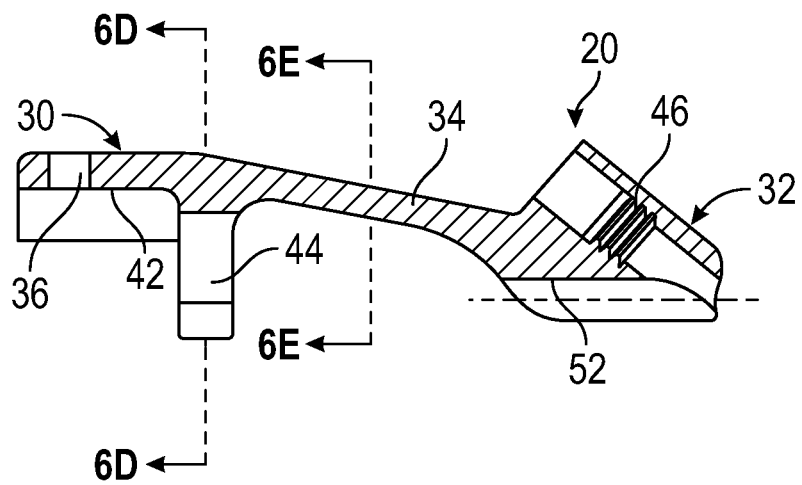
Figure 6C:
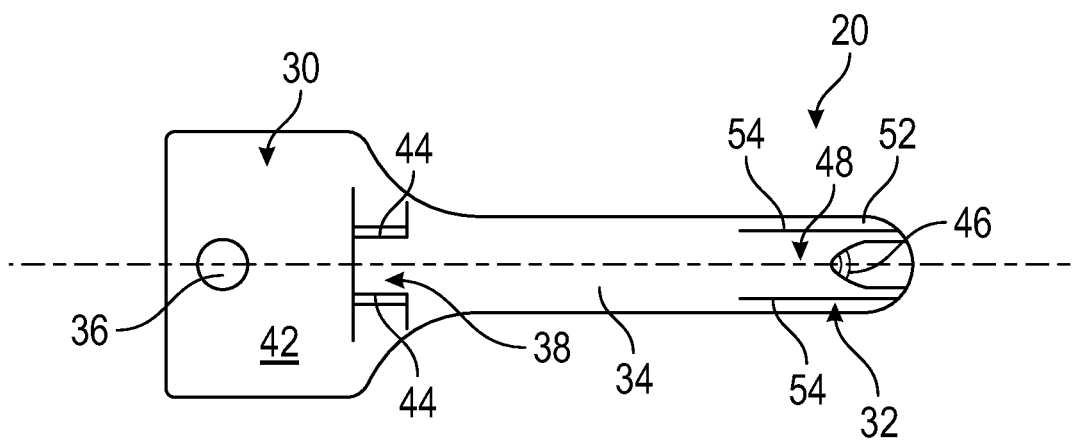
Figure 6D:
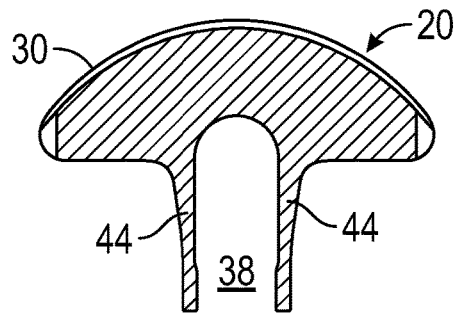
Figure 6E:
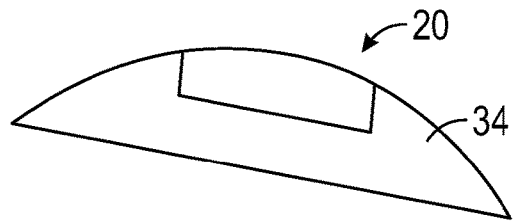
Figure 7A:
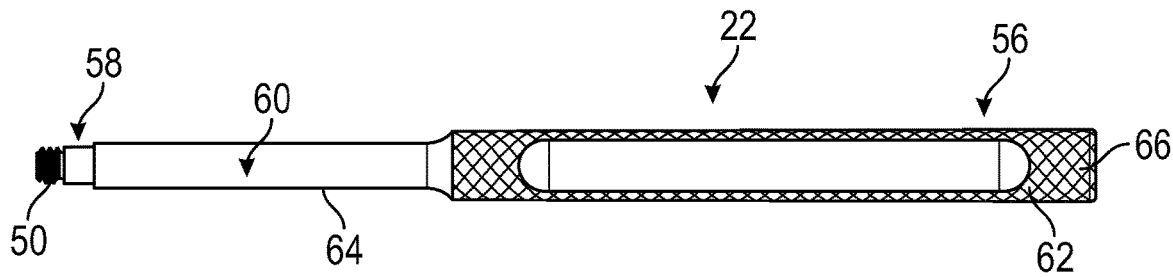
FIGS. 7A, 7B, and 7C illustrate an exemplary punch extension of a microfracture pick system.
Figure 7B:
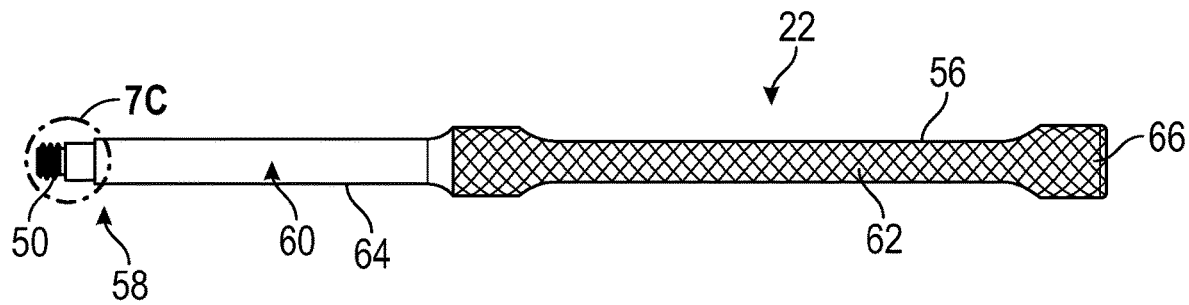
Figure 7C:
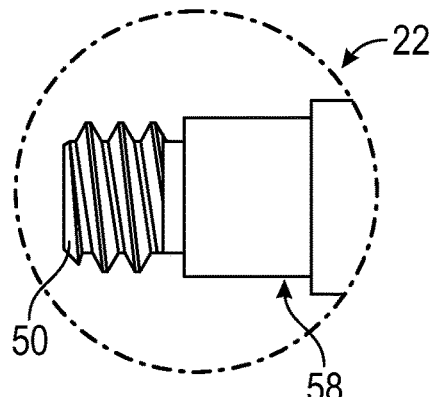

The microfracture pick 18 may include a handle 28, the shaft 26, and the strike tip 24. The shaft 26 may extend distally from the handle 28. The strike tip 24 may be integrally formed with the shaft 26 and may be relatively sharp. In an embodiment, the handle 28 and the shaft 26 both extend substantially along the longitudinal centerline axis A2, and the strike tip 24 extends substantially along the longitudinal centerline axis A3. The longitudinal centerline axis A3 may extend at an angle α relative to the longitudinal centerline axis A2. In an embodiment, the angle α is 30° (see FIG. 3). In another embodiment, the angle α is 60° (see FIG. 4). In yet another embodiment, the angle α is 90° (see FIG. 5). However, other angles are also contemplated within the scope of this disclosure. In another embodiment, portions of the shaft 26 may be curved and may extend non-linearly along the longitudinal centerline axis A2 (see, e.g., portion 55 of shaft 26 of FIG. 5).

Referring now to FIGS. 1, 2, and 6A-6E, the strike plate 20 may include a proximal portion 30, a distal portion 32, and a support arm 34 that extends from the proximal portion 30 to the distal portion 32. The proximal portion 30, the distal portion 32, and the support arm 34 may establish a unitary, single-piece body of the strike plate 20. The overall size and shape of the strike plate 20 are not intended to limit this disclosure. In an embodiment, the support arm 34 extends at a non-perpendicular angle relative to each of the proximal portion 30 and the distal portion 32.

The proximal portion 30 of the strike plate 20 may include a non-threaded through-opening 36 and a first slotted attachment portion 38. The non-threaded through-opening 36 may be configured to receive a pin 40 of the handle 28 of the microfracture pick 18 for connecting the strike plate 20 to the microfracture pick 18. In an embodiment, the pin 40 protrudes outwardly from a side surface of the handle 28 at a distal end portion of the handle 28. An opposite configuration is also completed in which a pin of the strike plate 20 is received within an opening of the handle 28 for securing the strike plate 20 to the microfractrue pick 18.

The first slotted attachment portion 38 may protrude outwardly from an inner surface 42 of the proximal portion 30. The shaft 26 of the microfracture pick 18 may be received between opposing arms 44 of the first slotted attachment portion 38 for securing the strike plate 20 to the microfracture pick 18.

The distal portion 32 of the strike plate 20 may include a threaded through-opening 46 and a second slotted attachment portion 48. The threaded through-opening 46 may be configured to receive a threaded tip 50 of the punch extension 22 for connecting the punch extension 22 to the strike plate 20. Once the threaded tip 50 is secured in the threaded through-opening 46, the punch extension 22 extends along the longitudinal centerline axis A1 that is transverse (e.g., non-perpendicular) to the longitudinal centerline axis A2 of the microfractrue pick 18 and is substantially axially aligned with the longitudinal centerline axis A3 of the strike tip.

The second slotted attachment portion 48 may protrude outwardly from an inner surface 52 of the distal portion 32. The shaft 26 of the microfracture pick 18 may be received between opposing arms 54 of the second slotted attachment portion 48 for securing the strike plate 20 to the microfracture pick 18. Therefore, via the non-threaded through-opening 36, the first slotted attachment portion 38, and the second slotted attachment portion 48, the strike plate 20 may be secured to both the handle 28 and the shaft 26 of the microfracture pick 18 and may be secured at least at two different locations of the shaft 26.

The strike plate 20 may be made from a metallic material, such as stainless steel, for example. However, other materials are also contemplated within the scope of this disclosure.

Referring now to FIGS. 1, 2, and 7A-7C, the punch extension 22 may include a proximal portion 56, a distal portion 58, and mid-portion 60 extending between the proximal and distal portions 56, 58. The proximal portion 56 may include a knurled surface 62 and an impact head 66. The impact force F may be applied to the punch extension 22 at the impact head 66. The distal portion 58 may terminate at the threaded tip 50. The mid-portion 60 may include a smooth cylindrical body 64.

The punch extension 22 may be made from a metallic material, such as stainless steel, for example. However, other materials are also contemplated within the scope of this disclosure.

A surgeon or other medical personnel may attach the strike plate 20 to the microfracture pick 18. This may include securing the strike plate 20 to the handle 28 via the pin 40 and the non-threaded through-opening 36 and/or securing the strike plate 20 to the shaft 26 via the first slotted attachment portion 38 and/or the second slotted attachment portion 48.

The surgeon/medical personnel may secure the punch extension 22 to the strike plate 20. This may include inserting the threaded tip 50 into the threaded through-opening 46. The microfracture pick system 10 is considered assembled when the strike plate 20 is attached to the microfracture pick 18 and the punch extension 22 is attached to the strike plate 20.

The impact head 66 of the punch extension 22 may be struck, such as with a surgical mallet, to generate the impact force F necessary for forcing the strike tip 24 through the bone surface 14 and into the underlying subchondral bone 16, thereby forming the microfracture 12.

The microfracture pick systems described herein may also be referred to as a surgical system or as a surgical kit. The exemplary microfracture pick systems of this disclosure provide a mechanical advantage for creating microfractures in bone during arthroscopic joint preparation by utilizing an off-axis impact design that substantially reduces the likelihood of the strike tip skiving along an irregular bony surface.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A microfracture pick system, comprising:
a microfracture pick;
a strike plate securable to a handle of the microfracture pick; and
a punch extension connectable to the strike plate and configured to apply an impact force to a portion of the microfracture pick,
wherein the strike plate comprises a unitary, single piece body that includes a proximal portion, a distal portion, and a support arm that extends from the proximal portion to the distal portion,
wherein the proximal portion of the strike plate includes a first slotted attachment portion, and further wherein a shaft of the microfracture pick is received between opposing arms of the first slotted attachment portion for securing the strike plate at a first shaft location of the microfracture pick.

2. The system as recited in claim 1, wherein the microfracture pick includes the handle, the shaft that extends from the handle, and a strike tip at a distal end portion of the shaft.

3. The system as recited in claim 2, wherein the punch extension extends along a first longitudinal centerline axis, the shaft of the microfracture pick extends along a second longitudinal centerline axis, and the strike tip extends along a third longitudinal centerline axis, and further wherein the first longitudinal centerline axis is transverse to the second longitudinal centerline axis and is substantially aligned with the third longitudinal centerline axis.

4. The system as recited in claim 1, wherein the system is configured such that the impact force is transferrable from the punch extension, through the strike plate, through the shaft of the microfracture pick, and then to a strike tip of the microfracture pick.

5. The system as recited in claim 1, wherein the distal portion of the strike plate includes a second slotted attachment portion, and further wherein the shaft of the microfracture pick is received between opposing arms of the second slotted attachment portion for securing the strike plate at a second shaft location of the microfracture pick.

6. The system as recited in claim 1, wherein the distal portion of the strike plate includes a second slotted attachment portion, and further wherein the shaft of the microfracture pick is received between opposing arms of the second slotted attachment portion for securing the strike plate to the microfracture pick.

7. The system as recited in claim 1, wherein the punch extension includes a proximal portion, a distal portion, and a mid-portion extending between the proximal and distal portions.

8. The system as recited in claim 7, wherein the proximal portion includes a knurled surface and an impact head.

9. The system as recited in claim 7, wherein the distal portion terminates at a threaded tip, and further wherein the threaded tip engages a threaded through-opening of the strike plate for connecting the punch extension to the strike plate.

10. The system as recited in claim 7, wherein the mid-portion includes a smooth cylindrical body.

11. The system as recited in claim 1, wherein the strike plate and the punch extension are made of stainless steel.

12. The system as recited in claim 1, wherein the strike plate is secured directly to the handle of the microfracture pick.

13. The system as recited in claim 1, wherein the strike plate is secured directly to both the handle and the shaft of the microfracture pick.

14. The system as recited in claim 1, wherein the strike plate includes a threaded through-opening configured to receive a threaded tip of the punch extension for connecting the punch extension to the strike plate.

15. The system as recited in claim 1, wherein a pin of the handle of the microfracture pick is received within a non-threaded opening of the strike plate to secure the strike plate to the handle.

16. A microfracture pick system, comprising:
a microfracture pick;
a strike plate securable to a handle of the microfracture pick; and
a punch extension connectable to the strike plate and configured to apply an impact force to a portion of the microfracture pick,
wherein the strike plate comprises a unitary, single piece body that includes a proximal portion, a distal portion, and a support arm that extends from the proximal portion to the distal portion,
wherein the proximal portion of the strike plate includes one of a non-threaded through-opening or a pin and the handle of the microfracture pick includes the other of the non-threaded through-opening or the pin, and further wherein the non-threaded through-opening is configured to receive the pin for connecting the strike plate to the handle of the microfracture pick.

17. A microfracture pick system, comprising:
a microfracture pick;
a strike plate securable to a handle of the microfracture pick; and
a punch extension connectable to the strike plate and configured to apply an impact force to a portion of the microfracture pick,
wherein the strike plate comprises a unitary, single piece body that includes a proximal portion, a distal portion, and a support arm that extends from the proximal portion to the distal portion,
wherein the distal portion of the strike plate includes a threaded through-opening configured to receive a threaded tip of the punch extension for connecting the punch extension to the strike plate.

\* \* \* \* \*